(12) United States Patent
Garcia-Rodenas et al.

(10) Patent No.: US 7,666,830 B2
(45) Date of Patent: *Feb. 23, 2010

(54) NUTRITIONAL COMPOSITION PREVENTING BACTERIAL OVERGROWTH

(75) Inventors: Clara L. Garcia-Rodenas, Forel (CH); Olivier Ballevre, Lausanne (CH); Florence Rochat, Montreux (CH)

(73) Assignee: Nestec S.A., Vevey (CH)

( * ) Notice: Subject to any disclaimer, the term of this patent is extended or adjusted under 35 U.S.C. 154(b) by 0 days.

This patent is subject to a terminal disclaimer.

(21) Appl. No.: 10/483,892

(22) PCT Filed: Jul. 25, 2002

(86) PCT No.: PCT/EP02/08336

§ 371 (c)(1),
(2), (4) Date: Jul. 29, 2004

(87) PCT Pub. No.: WO03/011055

PCT Pub. Date: Feb. 13, 2003

(65) Prior Publication Data

US 2004/0248768 A1    Dec. 9, 2004

(30) Foreign Application Priority Data

Jul. 30, 2001    (EP) ................................. 01118231

(51) Int. Cl.
*A61K 38/01* (2006.01)
(52) U.S. Cl. ............................ 514/2; 424/535; 435/68.1
(58) Field of Classification Search .................. None
See application file for complete search history.

(56) References Cited

U.S. PATENT DOCUMENTS

| | | | | |
|---|---|---|---|---|
| 5,039,532 A | * | 8/1991 | Jost et al. .................... 426/41 |
| 5,055,446 A | * | 10/1991 | Alexander et al. ............. 514/2 |
| 5,178,898 A | | 1/1993 | Juchem | |
| 5,230,902 A | * | 7/1993 | Gold et al. .................. 424/535 |
| 5,405,637 A | * | 4/1995 | Martinez et al. ............ 426/580 |
| 5,531,989 A | * | 7/1996 | Paul ......................... 424/93.4 |
| 5,661,123 A | | 8/1997 | Stalker et al. | |
| 5,821,217 A | | 10/1998 | Forse et al. | |
| 6,733,770 B1 | * | 5/2004 | Garcia-Rodenas et al. .. 424/439 |
| 6,887,850 B2 | * | 5/2005 | Fuchs et al. ................... 514/2 |

FOREIGN PATENT DOCUMENTS

| | | | |
|---|---|---|---|
| DE | 2845430 A | * | 4/1979 |
| EP | 488011 A2 | * | 6/1992 |
| EP | 0 626 177 A2 | | 11/1994 |
| EP | 0 671 126 A1 | | 9/1995 |
| EP | 1034704 A1 | * | 9/2000 |
| WO | WO 99/13738 | | 3/1999 |
| WO | WO 200054603 A1 | * | 9/2000 |

OTHER PUBLICATIONS

N. Chayen, "Protein crystallography: the human genome in 3-D." Physics World (1998) 8 pages.*
H. Berman, et al. American Scientist (2002) 90, pp. 350-359.*
M. Tomita, et al. J. Dairy Sci. (1991) 74, pp. 4137-4142.*
W. Brink. "Lactoferrin: The Bioactive peptide that fights disease." LifeExtension Magazine (2000), 7 pages.*
K. Yamauchi, et al. Infect. Immun. (1993) 61(2), pp. 719-728.*
PUBMED Accession No. AAA30617. Apr. 27, 1993, accessed Aug. 14, 2006. 1 page.*
Pepsin Digest of AAA30617 using "Peptide Cutter" by ExPASy. <<http://www.expasy.org/cgi-bin/peptidecutter/peptidecutterpl>> accessed Aug. 14, 2006. 6 pages.*
H. Saito, et al. J. Dairy Sci. (1991) 74, pp. 3724-3730.*
J. Rudinger. In: Peptide Hormones, JA Parsons, Ed. (1976) 1-7.*
Kops et al. article entitled "Partially Purified Soy Hydrolysates Retard Proliferation and Inhibit Bacteria Translocation in Cultured C2BBe Cells" *American Society for Nutritional Sciences*, 1997, pp. 1744-1751.
Teraguchl et al. article entitled "Orally Administered Bovine Lactoferrin Inhibits Bacterial Translocation in Mice Fed Bovine Milk" Applied and Environmental Microbiology, Nov. 1995, vol. 61, No. 11, pp. 4131-4134.

* cited by examiner

*Primary Examiner*—Andrew D Kosar
(74) *Attorney, Agent, or Firm*—K&L Gates LLP

(57) ABSTRACT

Protein hydrolyzates are used for prevention of bacterial overgrowth. In addition it was shown in sucklings mammals that specific protein hydrolyzates promote an intestinal flore pattern which is similar to the one of mammals raised by their mother. Other advantages are that the hydrolyzate is easier to obtain and simpler to administrate than treatment of bacterial overgrowth with the aid of active principles.

4 Claims, 4 Drawing Sheets

NUTRITIONAL COMPOSITION PREVENTING BACTERIAL OVERGROWTH

Figure 1:
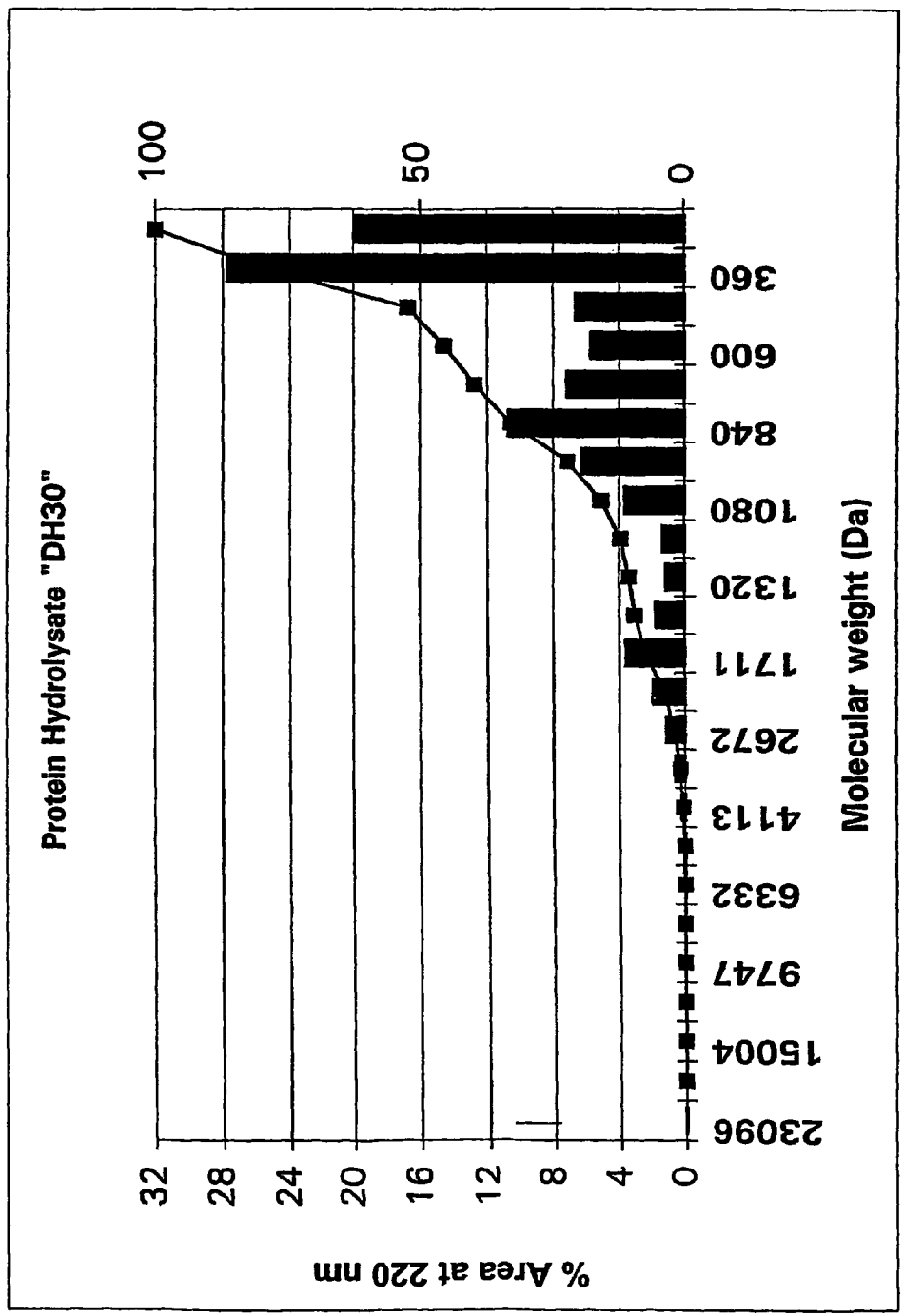

The present invention relates to the use of a nutritional composition preventing bacterial overgrowth, bacterial translocation and therewith linked disease like necrotizing enterocolitis, bacterial translocation septicemia and/or reduced availability of nutrients. The present invention also relates to a method for prevention or treatment of such conditions.

THE BACKGROUND ART

Bacterial overgrowth often occurs in preterm infants, critically ill patients and elderly and is one of the major causes of life-threatening events like nectrotizing enterocolitis, bacterial translocation, septicemia and reduced availability of nutrients.

In the earliest stages of bacterial overgrowth, bacteria that usually only inhabit the large intestine start to immigrate through the ileocecal valve and colonize the ileum. In a later stage, even the jejunum may be invaded. In general, colonization of the small intestine by bacteria is disadvantageous to the host, even in case of probiotic bacteria like certain *Lactobacillus* or *Bifodobacterium* strains that may have a beneficial impact to the host if present in the large intestine.

WO 200022945 (SOC PROD NESTLE SA) reports a new protein isolated from milk which has antiinflammatory, antibacterial and antiallergic properties and is therefore useful for preventing and treating inflammatory bowel disease, Crohn's disease, ulcerative colitis and other diseases.

JP 08059500 (MORINAGA MILK IND CO LTD) teaches a new mixture of peptides collected from lactoferrin hydrolyzates which has specific physicochemical and biological properties of preventing the migration of enteric bacteria from the intestine into other organs.

JP 05304929 (MORINAGA MILK IND CO LTD) discloses a way to improve abnormal bacterial compositions of human or animal intestine flora. The liquid or fluid food according to JP 05304929 contains bovine lactoferrin.

In general, protein hydrolyzates are well known and they are utilized in liquid formulas mainly to decrease allergenicity of the corresponding intact proteins. For example, milk protein hydrolyzates are part of nutritional formulas for people with allergy against antigens of milk proteins.

To date the problem of bacterial overgrowth is tackled by a drug therapy or, more recently, by other physiologically active substances that may be also isolated or purified from milk (e.g. lactoferrin). A drug therapy usually is not very advisable, because it means a strong impact on the body and also affects the bacterial flora of the colon. Hence, a drug therapy not just treats bacterial overgrowth, but annihilates the entire bacterial flora. The drawback of specific active principles, also those isolated from milk, is that they have to be produced or isolated and their uptake has to be exactly dosed, and, finally they may provoke side-effects, too. In addition, these substances are usually used only to treat advanced bacterial overgrowth and are not used for prevention purposes or for treatment of less severe conditions.

Therefore, there is a need for a natural, easy to produce product for the treatment of bacterial overgrowth, which does not involve an expensive purification procedure, which has at the same time nutritional value and which does not include side effects related to a drug therapy. In this sense, there is also a need for a mild treatment, which does not interfere with bacterial growth in the colon, where it is desirable.

After all, there is a need for a nutrient for the manufacture of a nutritional composition for suckling mammals, which promotes an intestinal flora pattern similar to the one present in mammals fed by their mother.

There is also a need of providing such nutrition based on unobjectionable and utilized food products instead of medication or in general pharmalogically active substances.

The present invention addresses the problem of providing nutrition to a patient suffering from bacterial overgrowth or translocation in the intestine and other diseases that are closely linked or direct consequences of bacterial overgrowth. The present invention also has the objective to provide the nutrition on the basis of unobjectionable and nutritionally valuable and advantageous nutrients and food.

It is also an aim of the present invention to provide nutrition to a patient suffering from bacterial overgrowth reducing the use of pharmaceutically active substances to the largest possible extent.

SUMMARY OF THE INVENTION

Remarkably, it has been found that specific protein hydrolyzates prevent bacterial overgrowth in small intestine and promote an intestinal flora pattern, which is similar to that induced by breast milk.

Consequently, in a first aspect the present invention provides the use of protein hydrolyzates for the preparation of a nutritional composition for preventing or treating bacterial overgrowth, necrotizing enterocolitis, bacterial translocation septicemia and/or reduced availability of nutrients.

In a second aspect the invention provides the use of protein hydrolyzates for the preparation of a nutritional composition for promoting or establishing a balanced and/or favorable intestinal flora pattern.

In a third aspect, the present invention provides a method for prevention or treatment of bacterial overgrowth or bacterial translocation, which comprises administering a nutritional composition comprising protein hydrolyzates.

In a forth aspect, the present invention provides a method for prevention or treatment of necrotizing enterocolitis, septicemia and/or reduced availability of nutrients, which comprises administering a nutritional composition comprising protein hydrolyzates.

An advantage of the present invention is that it provides a simple, readily available and inexpensive means for effectively preventing or treating bacterial overgrowth in intestine and other pathogenic conditions related therewith.

Another advantage of the present invention is that it provides prevention of bacterial overgrowth and at the same time is nutritionally valuable to the patient.

Yet another advantage of the present invention is that it is particularly suitable for preparing liquid formulas, for example enteral formulas.

In the figures,

FIG. 1 shows the molecular weight (MW) distribution of the protein hydrolyzate useful to carry out the invention. Bars represent the percentage of the total area measured at 220 nm that corresponds to the indicated MW range. The line represents the cumulative size distribution (% area vs MW). The median of the MW is at 475 Da (=MD 50%).

The peptide profile was assessed by size exclusion-high performance liquid chromatography (SEC-HPLC). A calibration curve of retention time versus molecular weight was performed using pure proteins, peptides and amino acids of known molecular weight (standards). At the wavelength of 220 nm peptide bonds as well as aromatic rigns of some amino acids are detected.

The vertical axis of FIG. 1 are named "% area at 220 nm", which reflects the fact that the irregular surface of the chromatogram is divided into various sections, based on the retention time of the standards, each one corresponding to a range of molecular weights. The surface of each section is divided by the total area (100%). It is a standard procedure for analysing molecular weight distribution.

Figure 2:
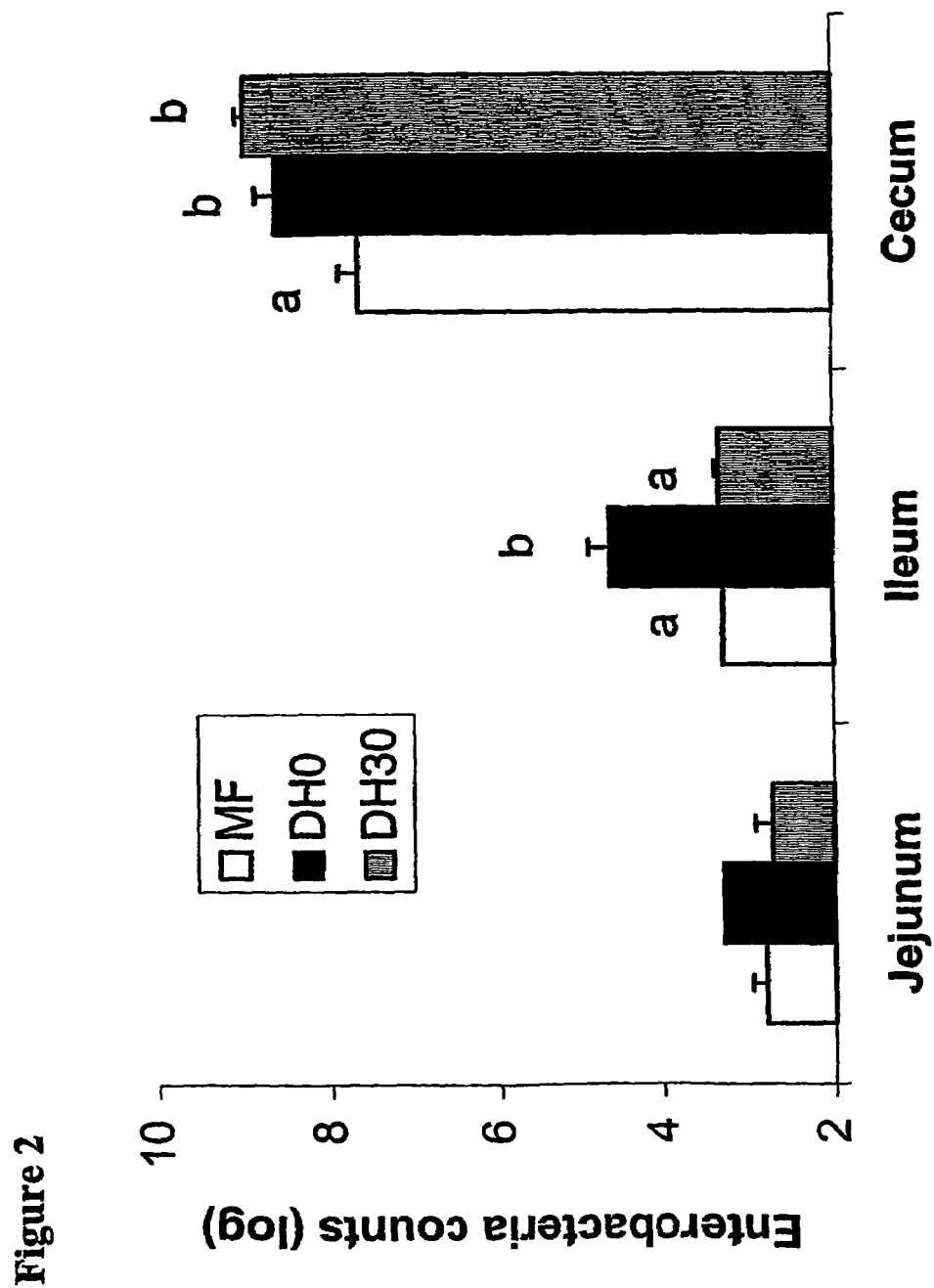

FIG. 2 shows Enterobacteria counts in jejunum, ileum and cecum of rats fet by their mother (MF, transparent bar) or with artificial diets (degree of hydrolysis (DH, see definition below) 0% and DH 30%, filled and striped bar, respectively). Average±Standard Errors (±SEM) values are presented. Within the same intestinal segment, different letters mean significant differences.

Figure 3:
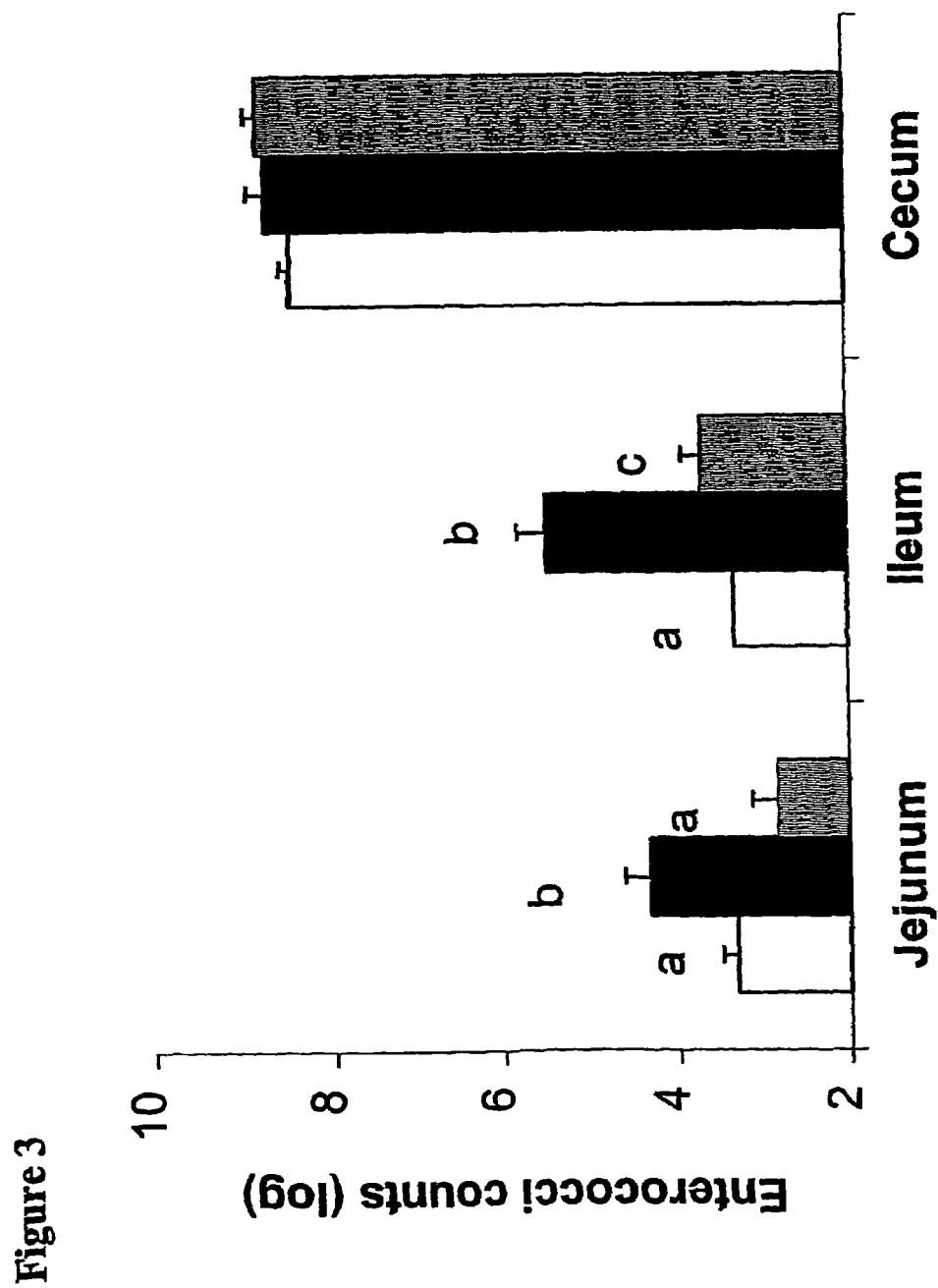

FIG. 3 shows Enterococci counts. Details see explanation of FIG. 2.

FIG. 3 shows Lactobacilli counts. Details see explanation of FIG. 2.

DETAILED DESCRIPTION OF THE INVENTION

Within the context of this specification the word "comprises" is taken to mean "includes, among other things". It is not intended to be construed as "consists of only".

Within the context of this specification the word "bacterial overgrowth" also refers to conditions of illness, malaise or indisposition related to or being the consequence of bacterial overgrowth. Septicemia and reduced availability of nutrients may serve as examples of such consequences.

Within the context of this specification the abbreviation "DH" refers to degree of hydrolysis. The term is well known in the art and denotes, in the context of proteinogenic matter, the percentage of $\alpha$-NH2-nitrogen with respect to total nitrogen (the amount of nitrogen that is in the form of free amino nitrogen). The unit (percentage) is sometimes omitted for reasons of convenience, especially where standard hydrolysates are used (e.g. DH0 refers to intact protein and DH30 refers to a extensively hydrolysed hydrolysate).

Nutritional compositions according to the use of the present invention may be produced according to common practice. Suitable compositions are known for other purposes, for example nutritional formulas for individuals suffering from food allergies as for milk protein or soy allergies. In general, the ingredients of the nutritional composition may be mixed in a dried form and then reconstituted in water, for example under stirring and/or heating.

Hence, any suitable protein source may be used for the production of the protein hydrolyzate according to the invention. Preferably, the protein source is a high quality protein source; for example milk protein, whey protein, casein protein, soy protein, meat-, fish- or poultry protein, or mixtures thereof may also be used.

More preferably, in an embodiment of the present invention the protein hydrolyzate is a milk protein hydrolyzate.

Preferably, the protein hydrolyzate is a whey protein hydrolyzate.

The protein hydrolyzate may be produced by any kind of hydrolysis. Preferably, it is produced by acid or enzymatic hydrolysis. The patent EP 322589 (SOCIETE DES PRODUITS NESTLE) discloses a process which is adequate to obtain a protein hydrolyzate within the meaning of the present invention. In addition, WO 9913738 (SOCIETE DES PRODUITS NESTLE) discloses a way for obtaining a particularly useful hydrolyzate. In example 1, under subtitle "Hydrolyzate 3", of this reference, the process protocol as well as an analysis of the resulting hydrolyzate is given.

Preferably, in an embodiment of the present invention, a degree of hydrolysis (DH) of the protein hydrolyzate is higher than 10%. Preferably, the degree of hydolysis is higher than 20%, more preferably it is higher than 30%.

Preferably, in an embodiment the degree of hydrolysis of the protein hydrolyzate is between 10% and 70%. More preferably, it is between 20% and 50%, more preferably between 25% and 35%. For example, the degree of hydrolysis of the protein is 30%. In case that a whey protein hydrolyzate is used, a degree of hydrolysis of 30% means that the major part of the protein matter is present in the form of dipeptides. Also tri- and oligo- and polypeptides as well as free amino acids may be present, however to a smaller extent as far as the number of molecules is concerned.

A protein hydrolyzate according to the present invention is also commercially available. For example, the whey protein hydrolyzate Lacprodam® DI-3065 of Arla Food Ingredients Ltd. may be used.

Preferably, the protein hydrolyzate is the only source of protein of the nutritional composition.

The protein source preferably provides about 1 to 50% of total caloric value of the nutritional composition. More preferably, it provides 10 to 30% total caloric value of the composition.

The nutritional composition may also comprise a lipid source. The amount of the fat or oil component may be adjusted to circumstantional factors, for example the condition of the patient and the presence of other diseases. The fat source may provide from 0 to about 50% of the total caloric value of the composition.

Preferably, it is present in an amount of 20 to 35% of total caloric value. The fat component can be any lipid or fat known in the art to be suitable for use in nutritional compositions. Typical fats include milk fat, safflower oil, canola oil, egg yolk lipid, olive oil, cotton seed oil, coconut oil, hazelnut oil, palm oil, palm kernel oil, and/or rapeseed oil. The fat source may include long- short and/or medium chain triglycerides (SCT, LCT, and/or MCT) in sufficient amounts. The lipids may consist of saturated, unsaturated, mono-, di-, tri- or poly-unsaturated fatty acids. Unsaturated fatty acids may be n-3 or n-6 fatty acids.

The nutritional composition may also comprise a carbohydrate source. The carbohydrate component may provide 5 to 90% of the total caloric value. Preferably, it comprises 20 to 55%, more preferably 40 to 50% of the energy. The carbohydrate source may be any suitable carbohydrate or carbohydrate mixtures. For example, the carbohydrate may be lactose, maltodextrin, modified starch, amylose starch, high amylose starch, topioca starch, corn starch, sucrose, galactose, glucose, fructose, or mixtures thereof. Hence, any poly-, oligo-, di-, and/or monosaccharides known to be suitable for use in nutritional formulas may be added.

In addition, the nutritional composition may comprise dietary fibre. Any suitable source of fibre may be used, depending on the circumstantional needs of the patient. Hence, soluble and insoluble fibre may be used, either alone or in combination. The soluble fibre may be a viscous fibre or a non-viscous fibre or a combination thereof. Possible sources of soluble fibres are guar gum, xanthan gum, gum arabic, pectin, β-glucan, inulin or mixtures of these. Suitable sources of insoluble fibre are hull fibres from legumes and grains; for example pea hull fibre, oat hull fibre, barley hull fibre, and soy hull fibre. However, any suitable source of insoluble dietary fibre may be used.

The nutritional composition preferably includes a complete vitamin and mineral profile. For example, sufficient vitamins and minerals may be provided to supply about 75 to about 250% of the recommended daily allowance of the vitamins and minerals per 1000 calories of the nutritional composition.

Various flavours, sweeteners and other additives may be present. For example, emulsifiers may be used.

If appropriate, the nutritional formula may also include functional ingredients. Depending on the condition of the patient, suitable plant extracts may be added. For example, plant extracts known to have beneficial effect on gut flora, constipation, diarrhoea and the like may be added. Examples are fennel, vervain, green tea, mint extract, prebiotic fibres, camomile, linden.

The nutritional composition conveniently has an osmolarity of about 180 mOsm/l to about 400 mOsm/l; for example about 250 mOsml/l to about 300 mOsm/l.

The energy density of the nutritional composition is preferably about 500 kcal/l to about 1500 kcal/l; more preferably from about 700 to about 1100 kcal/l.

The nutritional composition is preferably in the form of a ready to use formulation. In this form, the composition may be fed to a patient via a nasogastric tube, jejunum tube or by having the patient drink it. As such, the nutritional composition may be in a variety of forms; for example as a liquid infant formula, a fruit juice type beverage, a milk-shake type beverage and the like. However, the nutritional composition may be in a soluble powder form to be reconstituted prior to use.

With respect to the method of prevention or treatment of bacterial overgrowth, or the method for prevention or treatment of therewith associated diseases according to the present invention, the protein hydrolyzate preferably is the only source of proteinogenic matter. In an embodiment, the proteinogenic matter of a standard nutritional formula or of a food product is partly or totally replaced by the protein hydrolizate as defined within this description.

The nutritional composition may be produced according to standard practice; for example, by blending together the protein source, the carbohydrate source, and the lipid source. If used, the emulsifiers may be included in the blend. The vitamins and minerals may be added at this point but are usually added later to avoid thermal degradation. Any lipophilic vitamins, emulsifiers and the like may be dissolved into the lipid source prior to blending. Water, preferably water which has been subjected to reverse osmosis, may then be mixed in to form a liquid mixture. The temperature of the water may be conveniently about 50° C. to about 80° C. to aid dispersal of the ingredients. Commercially available liquefiers may be used to form the liquid.

The liquid mixtures may then be thermally treated to reduce bacterial loads. For example, the liquid mixture may be rapidly heated to a temperature in the range of 75° C. to about 110° C. for about 5 seconds to about 5 minutes. This may be carried out by steam injection or by heat exchanger; for example a plate heat exchanger.

The liquid mixture may then be cooled to about 60° C. to about 85° C.; for example by flash cooling. The liquid mixture is then homogenised; for example in two stages at about 7 MPa in the first stage and about 2 MPa to about 14 MPa in the second stage. The homogenized mixture may then be further cooled to add any heat sensitive components; such as vitamins and minerals. The pH and solid content of the homogenized mixture is conveniently standardised at this point.

For a product in liquid form, the homogenized mixture is preferably aseptically filled into suitable containers. Aseptic filling of the containers may be carried out by preheating the homogenized mixture (for example to about 75° C. to 85° C.) and then injecting steam into the homogenized mixture to raise the temperature to about 120 to 180° C.; more preferably to about 140 to 160° C. The homogenized mixture may then be cooled, for example by flash cooling, to a temperature of about 75 to 85° C. The homogenized mixture may then be further homogenized, cooled to about room temperature and filled into containers. Suitable apparatus for carrying out aseptic filling of this nature is commercially available.

For a product in powder form, the homogenised mixture is dried to powder; for example by spray drying. Conventional procedures may be used.

The nutritional composition may be used as a complete or a supplemental nutrition for patients suffering from bacterial overgrowth in the intestine, bacterial translocation, septicemia and reduced availability of nutrients. This diagnosis is often made with preterm or term newborns, infants, critically ill patients and the elderly. Furthermore, the nutritional composition may be used as a complete or a supplemental nutrition for preventing or treating bacterial overgrowth in the intestine, bacterial translocation, septicemia, and reduced availability of nutrients in preterm or term newborns, infants, critically ill patients and the elderly.

Without wishing to be bound by theory it is postulated that the beneficial effect of the protein hydrolyzate with respect to bacterial overgrowth is thougth to be linked to the high digestibility and rapid absorbtion of the protein hydrolysate. The fact that most of the proteinaceous material is present in small fractions, for example di-, tri-, or tetrapeptides, has the consequence that these are completely absorbed in the small intestine, even in patients with impaired gastrointestinal function. Would such patients or a preterm baby consume intact protein, this protein would not be entirely absorbed in the small intestine and would reach the lower end of the ileum. There the proteinaceous material may serve as a substrate for bacteria that usually do not colonise this area of the digestive tract in healthy individuals. It is therefore found that bacterial overgrowth may be prevented and cured by increasing the digestibility of the proteinaceous material, more specifically, by providing a protein hydrolyzate rather than intact protein to the affected individual. Again it is not proved that this explanatory model accounts totally for the surprising effects reported herein.

The following example is given by way of illustration only and in no way should be construed as limiting the subject matter of the present application. Percentages and parts are by weight unless otherwise indicated.

In the example a rat model is used, which does not reflect the identical situation found in humans and the results of which are therefore not directly and unequivocally transferable to humans. However, the model is selected on the basis of scientific research that acknowledges this rat model for studying the impact of nutritional interventions on immature digestive systems, like that of preterm babies, new-borns but also patients with digestive problems.

EXAMPLE

Effect of the protein source (intact vs. hydrolyzed whey protein) on the intestinal flora pattern of artificially reared suckling rats.

Methods

Animals and Diets

Sprague-Dawley rats were used in this study. Breeding mothers (purchased from Charles River Laboratories, Wilmington, Mass.) were housed individually in plastic cages and maintained under a 12-h dark/light cycle at 21±1° C. Animals had free access to 7002 Teklad 6% mouse/rat diet (Harlan Teklad, Madison, Wis.) and tap water. At day 4 after birth, 18 suckling rats were distributed into 2 experimental groups and then gastrostomized and artificially fed for 10 days. Ten littermates served as mother-fed control.

Diets

Animals were fed with two experimental milk formulas, having the same composition but for the protein source (table 1): 100% intact whey protein (DH 0%) and 100% extensive whey protein hydrolysate (DH 30%). The molecular weight distribution of the protein hydrolyzate is shown in FIG. 1.

TABLE 1

Composition of the experimental formulas employed during the artificial feeding

|  | DH 0 | DH 30 |
|---|---|---|
| Protein |  |  |
| DH0[1] | 8.3 g |  |
| DH30[2] |  | 10.0 g |
| Fat |  |  |
| Palm oil | 2.59 g | 2.59 g |
| Coconut oil | 2.16 g | 2.16 g |
| Soya oil | 1.73 g | 1.73 g |
| Table 1 (continued) |  |  |
| MCT oil | 1.29 g | 1.29 g |
| Cornoil | 0.87 g | 0.87 g |
| Cholesterol | 25 mg | 25 mg |
| Lecithin (topcithin) | 0.33 g | 0.33 g |
| Carbohydrate |  |  |
| Lactose | 2.2 g | 2.3 g |
| (Lactose from protein source) | (0.33 g) | (0.25 g) |
| Vitamins |  |  |
| Teklad vitamin mixture # 40060[3] | 0 | 0.33 g |
| Supplemental vitamin mixture[4] | 50 mg | 50 mg |
| Minerals |  |  |
| 1 N NaOH | 3.33 ml |  |
| 1 N KOH | 1.67 ml |  |
| Ca (lactate)2 | 0.258 g |  |
| Na2HPO4 | 0.167 g |  |
| Calcium glycerol phosphate | 1.02 g | 1.02 g |
| MgSO4 | 83 mg | 83 mg |
| CaCl2 | 55 mg |  |
| CuSO4 solution (30 mg/ml) | 0.05 ml | 0.05 ml |
| FeSO4 solution (30 mg/ml) | 0.083 ml | 0.083 ml |
| ZnSO4 solution (38 mg/ml) | 0.117 ml | 0.117 ml |
| MnSO4 solution (10 mg/ml) | 0.006 ml | 0.006 ml |
| NaF solution (10 mg/ml) | 0.013 ml | 0.013 ml |
| KI solution (10 mg/ml) | 0.015 ml | 0.015 ml |
| Distilled water | 91.3 ml | 91.3 ml |
| Protein (g/100 ml) | 6.7 | 6.7 |
| Fat (g/100 ml) | 9.2 | 9.2 |
| Carbohydrate (g/100 ml) | 2.5 | 2.5 |
| Energy content (Kj/100 ml) | 494 | 494 |

[1]DH0 = Intact whey protein (Globulal 80, Meggle, CH);
[2]DH30 = Extensive whey protein hydrolyzate (FIG. 1);
[3]Harlan Teklad Madison, WI, USA;
[4]Rivoflavin (16.7 g/Kg), niacin (26.0 g/Kg), pyridoxal (13.9 g/Kg), inositol (929.4 g/Kg), and asorbic acid sodium salt (14.0 g/Kg)

Experimental Protocol

All procedures used in this protocol were reviewed and approved by the Animal Care Committee at the University of Arizona. Four day-old suckling rats were anesthetized and gastrostomized with a polyethylene cannula with a hook-shaped end (PE-20, Clay Adams/Benton Dickinson and Co., Parsippany, N.J.). Following postsurgical recovery, which included a 2 h fast, pups were weighed and the volume of artificial formula to be given to each animal calculated to deliver approximately 35-37% of body weight per 24 h period. Pups were placed in plastic cups and floated in a 39° C. water bath for the duration of the feeding study to maintain the ambient temperature and humidity. The gastrostomy tubes were connected to syringes on Model 44 Harvard in fission pumps (Harvard Apparatus, South Natick, Mass.) in a refrigerator by means of SILASTIC® tubing (Dow Corning Corp., Midland, Miss.). Pumps were set to deliver the calculated volume of diet for 20 min followed by 40 min pause each hour. The volume of diet to be delivered was recalculated daily. Each day body weights, eye opening, and tail lengths were recorded. Two times daily, urination and defecation were induced by gentle stimulation of the anogenital region.

At day 14, pups were sacrificed by decapitation. The gastrointestinal tract was quickly removed on sterile conditions and excised into duodenum (1 cm from pylorus), jejunum, ileum (half-proximal and distal parts of the remaining small intestine, respectively) and cecum. Jejunum and ileum were each washed with 1 ml sterile ice-cold 0.9% NaCl, 10% glycerol solution. Contents were directly collected and weighed in NUNC® (Nalgene) sterile tubes. Cecum was opened, contents removed with a sterile spatula and weighed inside a NUNC® tube, to which 1 ml of NaCl+glycerol solution was then added. Intestinal contents were immediately frozen in liquid nitrogen.

Analysis of the Flora in the Intestinal Contents

Flora (bifidobacteria, lactobacilli, enterococci, enterobacteria and Clostridium perfringens) in jejunal, ileal and cecal contents was assessed by plating on selective or semi selective media.

Hundred fold serial dilutions were performed in Ringer solution containing 0.5% of cystein, from −2 to −8. Petri dishes of various selective media were inoculated and incubated (see Table 2).

TABLE 2

Conditions for the cultivation of specific strains

| Bacteria | Media | T (° C.) | Time (h) | Atmosphere |
|---|---|---|---|---|
| Enterobacteriaceae | Drigaiski (Sanofi Diagnostics Pasteur, France) | 37 | 24 | Aerobic |
| Bifidobacteria | Eugon Tomato* | 37 | 48 | Anaerobic |
| Lactobacilli | MRS (Difco, MI. USA) + antibiotics** | 37 | 48 | Anaerobic |
| Cl.perfringens | NN Agar*** | 37 | 48 | Anaerobic |
| Enterococci | Azide Agar (Difco) | 37 | 24 | Aerobic |

*: Wadsworth Anaerobic Bacteriology Manual, V. Suter, D. Citron and S. Finegold Third ed.
**: Phosphomycine (79.5 mg/l) + Sulfamethoxazole (0.93 mg/l) + Trimethoprime (5mg/l)
***: NN agar from Lowbury and Lilly, 1995

The anaerobic atmospheric was obtained using an ANAEROCULT® A gas-generating system (MERCK, Darmstadt, Germany). After incubation, the colonies were counted and further identified if necessary. Lactobacilli and Bifidobacteria strains were identified by microscopy, and enzymatic activities. Counts are expressed as cfu/g of fresh fecal sample with a detection limit at 3.30 cfu/g, and expressed as log.

Statistical Analysis

Due to the nulle variability observed in some of the groups, a classical analysis of the variance (ANOVA) could not be performed. A Wilcoxon rank test for group pairs was employed instead. Mean differences with p values lower than 0.05 were considered as significant.

Results

Figure 4:
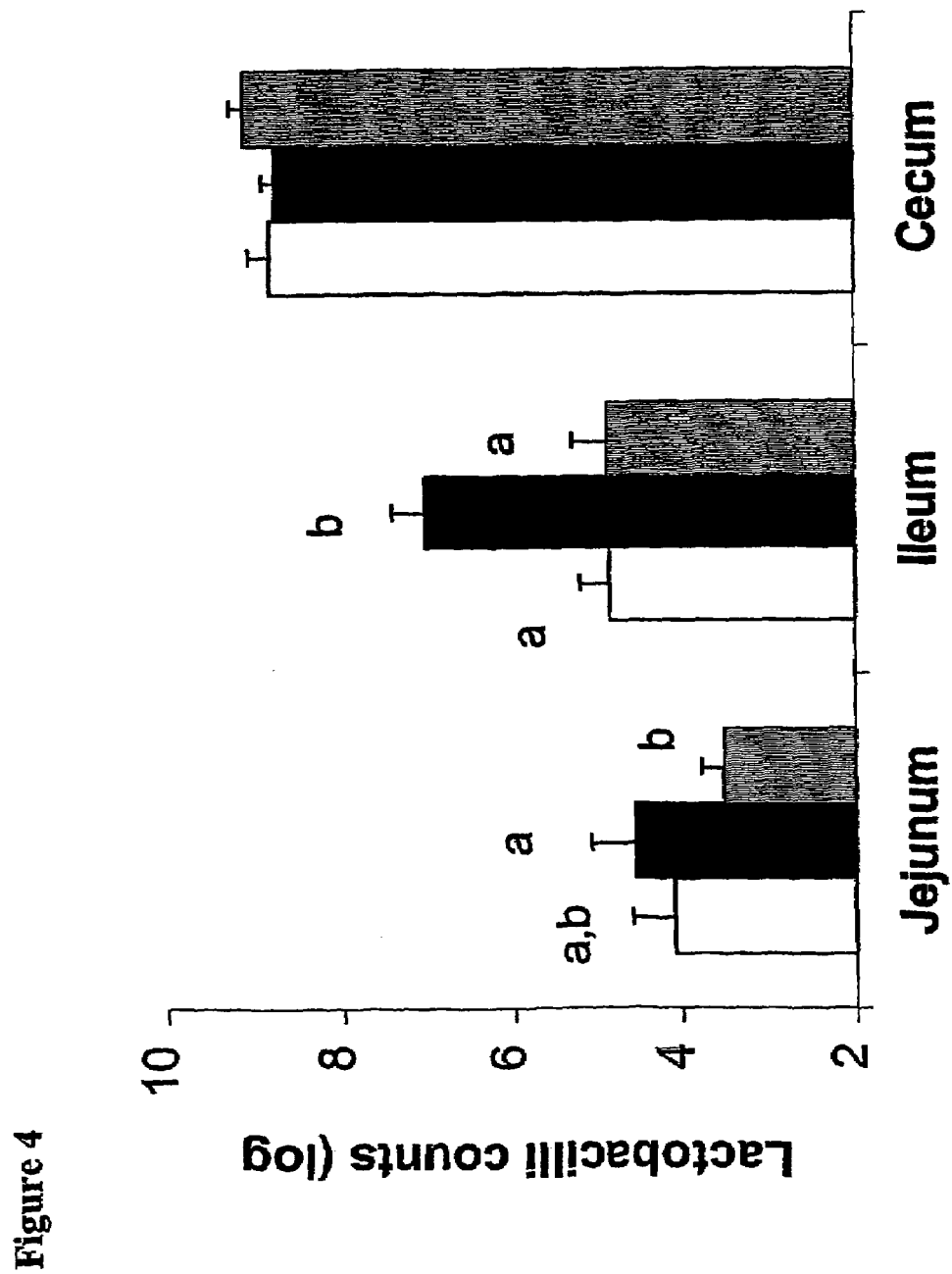

FIG. 2-4 show the counts of enterobacteria, enterococci and lactobacilli in the contents of the different intestinal segments.

Enterobacteria counts in ileum were higher in DH0 than in the other groups. DH30 and MF resulted in similar values, at the detection limit. In cecum the only distinct group was MF, with smaller counts.

Enterococci were much more abundant in jejunum and ileum with DH0 than with DH30 or MF. No significant differences within diets were observed in cecum.

Lactobacilli in ileum were more abundant in DH0 than in the other groups. A similar trend was found in jejunum, although in that case MF showed values placed in between DH0 and DH30. Again, no differences were detected in cecum.

Bifidobacteria was not detected in either group or intestinal segment. Concerning Clostridium, only four animals (two in DH0 and two in MF) had detectable values in cecum and one animals in ileum (in DH0). Those values were considered negligible and no stastistical comparison was made between diets.

Conclusions

Feeding with intact whey protein promoted bacterial overgrowth in small intestine of the pups. This overgrowth was prevented in a great extend by feeding extensive whey protein hydrolyzate, which resulted in flora patterns rather similar to those observed after mother feeding.

Protein hydrolyzates are therefore a useful means for preventing or treating bacterial overgrowth and therewith associated diseases. It is possible to restore an intestinal flora pattern that is similar to the one of individuals nourished with mother milk.

It should be understood that various changes and modifications to the presently preferred embodiments described herein will be apparent to those skilled in the art. Such changes and modifications can be made without departing from the spirit and scope of the present invention and without diminishing its attendant advantages. It is therefore intended that such changes and modifications be covered by the appended claims.

What is claimed is:

1. A method for treating and reducing bacterial overgrowth or translocation, the method comprising the step of administering to an individual having bacterial overgrowth or translocation a nutritional composition comprising as a sole source of protein a whey protein hydrolysate, wherein the degree of hydrolysis of the whey protein hydrolyzate is greater than 30%.

2. A method for the prevention of necrotizing enterocolitis, septicemia and/or reduced availability of nutrients, comprising the step of administering to an individual at risk of same a nutritional composition comprising as a sole source of protein a whey protein hydrolyzate, wherein the degree of hydrolysis of the whey protein hydrolyzate is greater than 30%.

3. A method for treating and reducing bacterial overgrowth or translocation, the method comprising the step of administering to an individual in need of same a therapeutically-effective amount of a nutritional composition comprising as a sole source of a protein a whey protein hydrolysate, wherein the degree of hydrolysis of the protein hydrolyzate is greater than 30%.

4. A method for the treatment of necrotizing enterocolitis, septicemia and/or reduced availability of nutrients, comprising the step of administering to an individual suffering from same a therapeutically-effective amount of a nutritional composition comprising as a sole source of protein a whey protein hydrolyzate, wherein the degree of hydrolysis of the whey protein hydrolyzate is greater than 30%.

* * * * *